United States Patent [19]

Charlebois et al.

[11] 4,107,465
[45] Aug. 15, 1978

[54] AUTOMATIC AUDIOMETER SYSTEM

[75] Inventors: Jacques Charlebois; Guy Lescouflair, both of Sainte-Foy, Canada

[73] Assignee: Centre de Recherche Industrielle du Quebec, Quebec, Canada

[21] Appl. No.: 863,238

[22] Filed: Dec. 22, 1977

[51] Int. Cl.$^2$ .......................... H04R 29/00
[52] U.S. Cl. .................................... 179/1 N
[58] Field of Search ................... 179/1 N, 107

[56] References Cited

U.S. PATENT DOCUMENTS

| 3,809,811 | 5/1974 | Delisle | 179/1 N |
| 4,038,496 | 7/1977 | Feezor | 179/1 N |

Primary Examiner—Thomas W. Brown
Assistant Examiner—E. S. Kemeny
Attorney, Agent, or Firm—Charles E. Brown

[57] ABSTRACT

An audiometer for testing the hearing characteristic of a person. The audiometer is entirely operable by the user whereby technicians are not required. The audiometer comprises a source of audible and selectable fixed frequency signals. An automatic frequency selector switch selects a predetermined frequency signal from the source. A variable attenuator circuit is provided to automatically attenuate, in sequence, the predetermined frequency through a plurality of attenuation levels and according to a preselected mode of operation whereby to transmit a plurality of attenuated frequency signals. The attenuated frequency signals are transmitted for audible reception by the person using the audiometer. Visual display lamps indicate the test frequencies and attenuation, permitting the user to fill out a test chart on corresponding sounds audible to his ears. A control circuit is provided to enable the frequency selector means and the variable attenuator in accordance with a preselected mode of operation.

20 Claims, 4 Drawing Figures

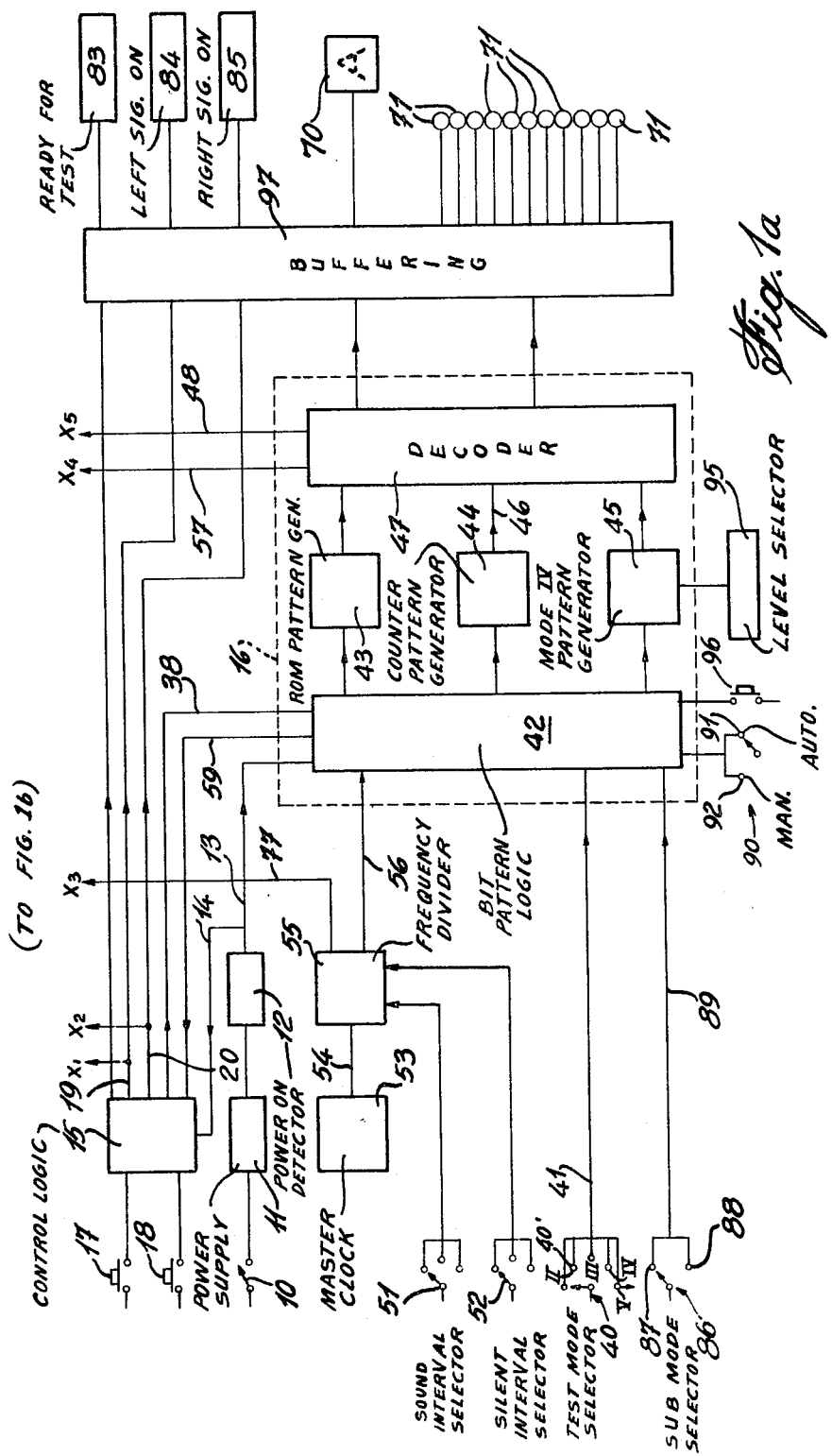

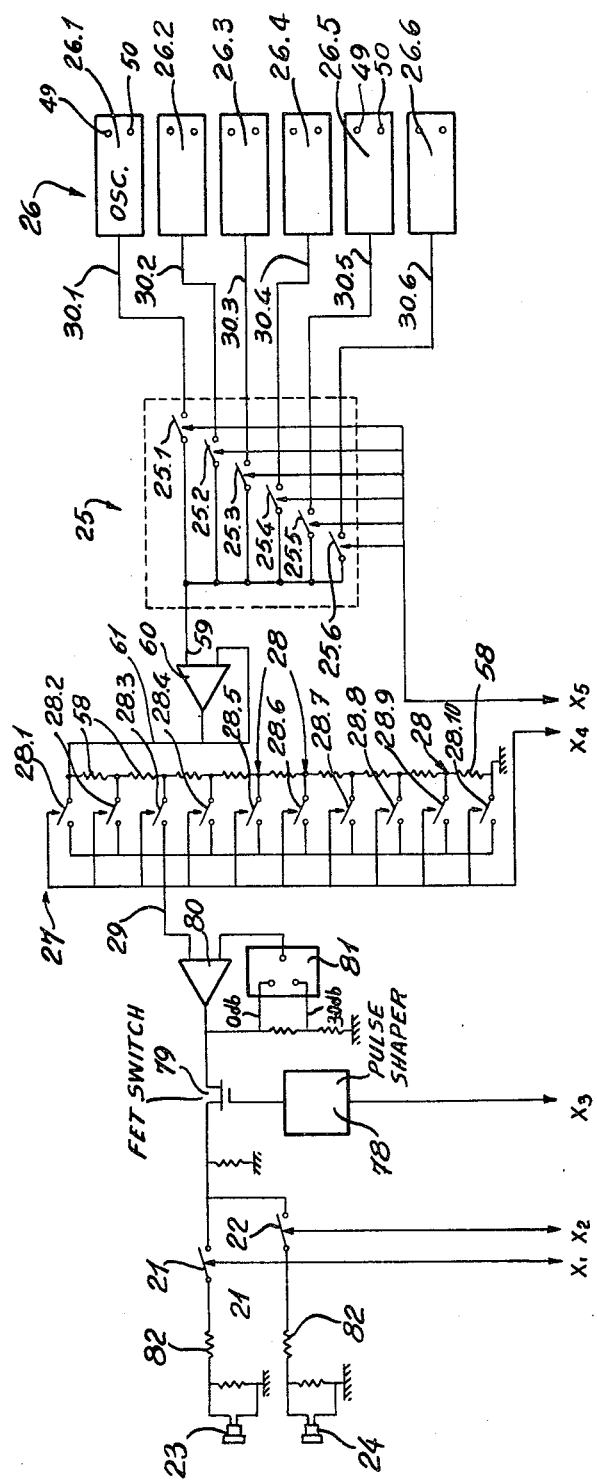

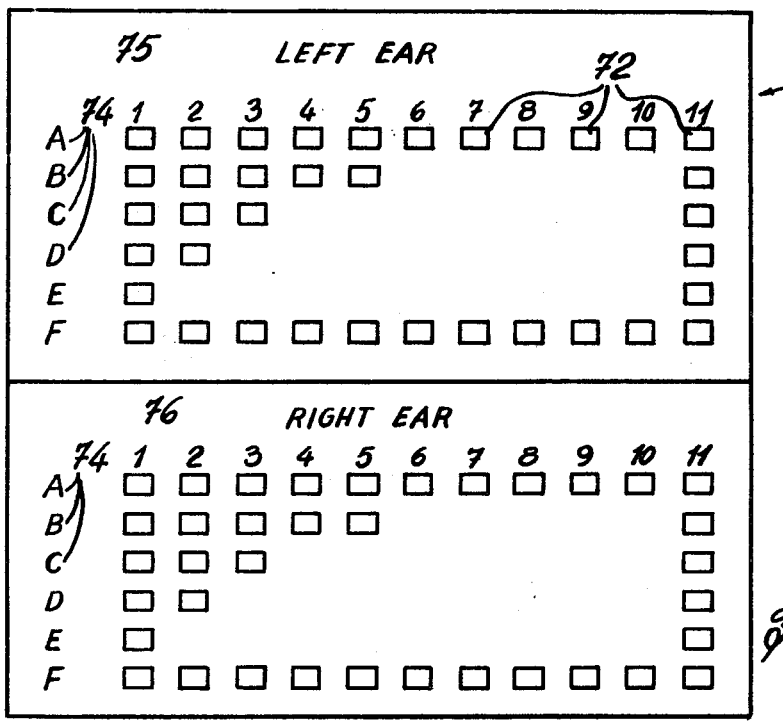

| MODE I SINGLE Fr. | | | MODE II DESCENDING | | | | MODE III RANDOM | | | | MODE IV RAPID | | | | MODE V CALIBRATION | | | |
|---|---|---|---|---|---|---|---|---|---|---|---|---|---|---|---|---|---|---|
| f | LAMP | dB | f | LAMP | LETTER | dB | f | LAMP | LETTER | dB | f | LAMP | LETTER | dB | f | LAMP | LETTER | dB |
| 4K | 9 | 50 | 1K | 9 | A | 50 | 1K | 11 | A | 50 | 1K | | A | 20 | 1K | | A | 80 |
|  | 8 | 45 |  | 8 |  | 45 |  | 10 |  | 35 | 2K | | B | 20 | 2K | | B | 80 |
|  | 7 | 40 |  | 7 |  | 40 |  | 9 |  | NIL | 4K | NONE | C | 20 | 4K | NONE | C | 80 |
|  | 6 | 35 |  | : |  | : |  | 8 |  | 25 | .5K |  | D | 25 | .5K |  | D | 80 |
|  | 5 | 30 |  | : |  | : |  | 7 |  | 40 | 3K |  | E | 20 | 3K |  | E | 80 |
|  | 4 | 25 |  | 1 |  | 10 |  | 6 |  | 45 | 6K |  | F | 20 | 6K |  | F | 80 |
|  | 3 | 20 | 2K | 9 | B | 50 |  | 5 |  | 10 | | | | | | | | |
|  | 2 | 15 |  | 8 |  | 45 |  | 4 |  | NIL | | | | | | | | |
|  | 1 | 10 |  | : |  | : |  | 3 |  | 30 | | | | | | | | |
|  |  |  |  | 1 |  | 10 |  | 2 |  | 15 | | | | | | | | |
|  |  |  | 4K | : | C |  |  | 1 |  | 20 | | | | | | | | |
|  |  |  | .5K |  | D |  | 2K | 11 | B | 50 | | | | | | | | |
|  |  |  | 3K |  | E |  |  | 10 |  | 45 | | | | | | | | |
|  |  |  | 6K |  | F |  |  | 9 |  | 10 | | | | | | | | |
|  |  |  |  |  |  |  |  | 8 |  | 35 | | | | | | | | |
|  |  |  |  |  |  |  |  | 7 |  | NIL | | | | | | | | |
|  |  |  |  |  |  |  |  | 6 |  | 20 | | | | | | | | |
|  |  |  |  |  |  |  |  | 5 |  | NIL | | | | | | | | |
|  |  |  |  |  |  |  |  | 4 |  | 40 | | | | | | | | |
|  |  |  |  |  |  |  |  | 3 |  | 25 | | | | | | | | |
|  |  |  |  |  |  |  |  | 2 |  | 30 | | | | | | | | |
|  |  |  |  |  |  |  |  | 1 |  | 15 | | | | | | | | |
|  |  |  |  |  |  |  | 4K | 11 | C | 50 | | | | | | | | |
|  |  |  |  |  |  |  |  | 10 |  | 40 | | | | | | | | |
|  |  |  |  |  |  |  |  | 9 |  | 25 | | | | | | | | |
|  |  |  |  |  |  |  |  | 8 |  | NIL | | | | | | | | |
|  |  |  |  |  |  |  |  | 7 |  | 20 | | | | | | | | |
|  |  |  |  |  |  |  |  | 6 |  | 35 | | | | | | | | |
|  |  |  |  |  |  |  |  | 5 |  | 15 | | | | | | | | |
|  |  |  |  |  |  |  |  | 4 |  | 45 | | | | | | | | |
|  |  |  |  |  |  |  |  | 3 |  | 30 | | | | | | | | |
|  |  |  |  |  |  |  |  | 2 |  | NIL | | | | | | | | |
|  |  |  |  |  |  |  |  | 1 |  | 10 | | | | | | | | |
|  |  |  |  |  |  |  | .5K | SAME AS 1K | D | SAME AS 1K | | | | | | | | |
|  |  |  |  |  |  |  | 3K | SAME AS 2K | E | SAME AS 2K | | | | | | | | |
|  |  |  |  |  |  |  | 6K | SAME AS 4K | F | SAME AS 4K | | | | | | | | |

Fig. 3

AUTOMATIC AUDIOMETER SYSTEM

BACKGROUND OF THE INVENTION

1. Field of the Invention

The present invention relates to an improved audiometer system which is entirely operable by the user whereby he can self-test his hearing acuity for different frequencies without the assistance of an operator for adjusting the test instrument or for recording the user's responses.

2. Description of Prior Art

Known audiometers are of two main types: the manual and the so called automatic type. In the manual system and method of auditory testing, a skilled operator adjusts the audiometer controls, thereby sending a plurality of audio signals either through earphones, loudspeakers or bone vibrators, to a subject generally sitting in a quiet room. The subject is requested to signal to the operator, either by activating a switch connected to a pilot light, or by raising his hand or by any other visible or audible means, whenever he has heard the sound being sent to him. The operator watches for and interprets the subject's responses and translates them into written information on a chart, this information being represented by a graph called the audiogram which represents the threshold of hearing of the subject for a plurality of audio frequencies.

In the automatic method known as the Bekesy method of auditory testing, the audiometer presents to the subject automatically changing tone frequencies while the intensity of the signal is controlled by the subject by means of a pushbutton switch activating a motor controlling the motion of an intensity attenuator. The subject's responses are also automatically recorded by means of a writing pen moving over a chart as the test progresses. While the Bekesy method is considered by those skilled in the art of audiology as a major advance, it still requires the presence of a skilled operator and the use of rather sophisticated mechanical systems.

A further method of auditory testing has been proposed in which a computer is used to present the tones to the subject in a programmed sequence and record his responses. Reference is made to U.S. Pat. No. 3,809,811 and Canadian patent 950,106. In this type of instrument, the triggering of different intensities and frequencies by the programming circuit is entirely dependent upon the feedback from the subject's responses, through his actuation of a "YES" button, but calling for a relatively complex electronic circuitry.

There exists in industry a need to have an equipment which allows a rapid test of hearing at the time of hiring a new employee to establish his basic status of hearing thereby warning the employer of any hearing loss that may already be present and possibly gone undetected previously and protecting the employer against later claims of hearing loss that would be attributed to his industry's noise. It must be possible to execute such a pre-employment test at the earliest possible time without having to wait for the availability of an operator.

Also, in noisy industrial settings there exists a need to administer periodical hearing tests to employees with minimum lost time away from work. Such a requirement is not easily possible to fulfil with instruments of prior art which usually have to be installed in quiet rooms away from the work premises.

In audiometric methods of prior art, it is quite possible for the subject being tested to deliberately give false responses which might be interpreted by the operator as reflecting the true condition of the hearing acuity of the subject. For instance, new job applicants in industry who are already partially hard of hearing might try to falsify the test by pretending that they heard all the tones presented to their ears, by fear of not being employed if the employer was made aware of their true hearing loss. On the other hand, old employees might pretend of being more hard of hearing than they are in reality, in the hope of obtaining compensation for industrial hearing loss.

SUMMARY OF INVENTION

A feature of the present invention is that it permits administration of an auditory test in an entirely automatic manner which does not require the presence of any operator but the user himself. Moreover, the auditory signals are applied according to predetermined fixed parameters which are entirely independent from the subject's responses and not meant to be influenced by them. Thus the electronic and mechanical complexity of the apparatus is considerably reduced. Since the apparatus of the present invention contains very few mechanical moving parts, it is less prone to failure as it is well known that audiometer failure is most frequently due to failure of mechanical moving parts.

A further feature is that the simplicity of the system of the present invention coupled with the elimination of the necessity of an operator makes it readily affordable costwise to organizations concerned with the prevention of hearing loss and the surveillance of auditory acuity of large groups of people such as noisy industries, public and school health organizations. Known audiometers, especially of the automatic type, are relatively expensive and since they require the presence of an operator, testing the hearing acuity of a subject can be a relatively costly operation.

A still further feature of the present invention is to provide a genuine approach to the early prevention of hearing loss. For example, in school systems, there exists a need to test the hearing acuity of school children first at the time of their entrance into the school system and periodically thereafter to monitor any loss of hearing which may adversely affect their learning progress and social behaviour. Known methods of school hearing screening have so far utilized the services of a skilled operator travelling from school to school with a portable audiometer. Such a method is relatively inefficient both costwise and as far as early prevention is concerned compared to a method and system as proposed in the present invention which allows a constant monitoring of all school children's hearing when the apparatus is permanently installed on the premises.

A further feature of the system of the present invention is that the audiometer may be installed close to work quarters and used by employees at any convenient moment with minimum lost time away from work. A worker in a noisy environment may thus be able to test his hearing acuity for high frequencies, those primarily susceptible to be affected by noise exposure, without being required to be in a special audiometric quiet room, nor rely on the presence of an operator nor leaving the work premises. Such a test may be executed by the worker as many times as he wishes from day to day, thereby warning him of any deterioration of his hearing acuity attributable to noise exposure. Thus the present invention provides the added advantage of inducing a better motivation for self-protection among employees.

A still further feature of the present invention is to proivde means of defeating audiometric malingering. Malingerers can be immediately detected through the use of one particular feature of the present invention which provides a means of presenting the tones in a randomly attenuated manner, thereby depriving the would-be malingerer or exaggerator of any clue as to the level of the signal being presented to him.

Another feature of the present invention is that it is inexpensive and does not require a special room for a person to undergo testing.

A further feature of the present invention is to provide an audiometer having a plurality of modes of operation whereby tones of either constantly decreasing or variable random levels may be transmitted to each ear of a person undergoing tests to determine his hearing acuity.

A further feature of the present invention is to provide an audiometer which substantially overcomes the disadvantages of the prior art.

According to the above features, from a broad aspect, the present invention provides an audiometer for testing the hearing of a person. The audiometer comprises a source of audible and selectable fixed frequency signals. Frequency selector means is provided for selecting a predetermined frequency signal from this source. A variable attenuator circuit is provided and has a plurality of attenuation levels for automatically attenuating the predetermined frequency signal through the attenuation levels and according to a preselected mode of operation for transmission of a plurality of attenuated frequency signals. Means is further provided to transmit the attenuated frequency signals for audible reception by the person using the audiometer. Visual display means indicates the transmission of each of the attenuated frequency signals or steps of attenuation. Control circuit means enables the frequency selector means and the variable attenuator in accordance with the preselected mode of operation.

According to a further broad aspect of the present invention, there is provided a method of testing the hearing of a person and which comprises the steps of automatically selecting, in a preselected mode of operation, a plurality of fixed frequency signals. Each of the frequency signals is automatically attenuated to predetermined attenuating levels preselected in accordance with the said mode of operation to produce a plurality of attenuated frequency signals. Each of the attenuated frequency signals is transmitted to a selected one of the person's ears to provide to the person a means of self-determining his auditory acuity for each ear. A selected one of the fixed frequency signals and each of the attenuated frequency signals or steps of attenuation being transmitted, are visually indicated on the audiometer.

BRIEF DESCRIPTION OF DRAWINGS

A preferred embodiment of the present invention will now be described with reference to the accompanying drawings in which:

FIGS. 1a and 1b are detailed block diagrams showing the construction of the electrical circuits constituting the audiometer;

FIG. 2 is a plan view illustrating a test chart; and

FIG. 3 is a table illustrating the five modes of operation of the audiometer.

BRIEF DESCRIPTION OF PREFERRED EMBODIMENT

Referring now to FIGS. 1a and 1b, there is shown the interconnection of the various circuits which constitutes the audiometer system of the present invention. A power switch 10 is provided on the console (not shown) of the audiometer to switch on the power supply 11 which feeds a power-up detector 12. The power-up detector 12 senses the supply voltage from the power supply 11 and produces a "power-up reset" pulse at its output 13. This power-up reset pulse is applied to all bistable elements within the system. A connection 14 from the output of the detector 12 feeds a control logic circuit 15 which in turn enables a bit pattern generator 16, (herein the control circuit means of the system), through connection 38, when the right ear switch 17 or left ear switch 18 is depressed by the person using the audiometer. Further, when the switch 17 or 18 is depressed, a switch activation signal is sent out on one of the outputs 19 and 20 of the control logic circuit 15 to cause actuation of an analog switch 21 or 22 which switches in the system a left earphone 23 or right earphone 24, respectively.

When one of the switches 17 and 18 is depressed, the bit pattern generator circuit 16 enables a frequency selector circuit 25 in accordance with a preselected mode of operation for the system. The output frequency tone selected is then fed to a variable attenuator circuit 27 to produce at its output 29 a plurality of attenuated frequency signals depending on the number of attenuation levels 28 applied to the selected frequency signal. After the signal is subjected to all predetermined attenuations, a further signal from the frequency source is then subjected to attenuations. The selection of frequencies and attenuation levels for each frequency is predetermined by the mode of operation.

Before the audiometer is used by a person to undergo auditory tests, the audiometer is calibrated and set to operate in one of five available modes of operation. These modes are shown in the table illustrated by FIG. 3. A mode selector switch 40 is utilized for this purpose and it is shown as in its position I where the control circuit 16 will cause the system to generate a 4 KHz frequency attenuated in sequence from 50 dB down to 10 dB attenuation in accordance with ANSI Standard S3.6-1969 (R1973). The output 41 of the mode selector switch 40 is connected to a bit pattern logic circuit 42 in the control circuit 16. This bit pattern logic circuit will select one of the pattern generators 43, 44 or 45 which is associated with mode I. Herein, the pattern generator circuit 44 controls modes I, II and V. Mode III is controlled by pattern generator circuit 43 and mode IV is controlled by pattern generator circuit 45, which modes will be described in more detail later.

The output 46 of the pattern generator 44 is connected to a decoder circuit 39 which will cause the proper selection of the frequency by selecting a predetermined one of the switches 25.1 to 25.6 of the frequency selector circuit 25 by sending a proper signal at its output 48 to the frequency selector. In this particular case, switch 25.5 of the frequency selector will be enabled whereby to connect the 4 KHz sinusoidal oscillator 26.5 from the frequency source 26.

The frequency source 26 consists of six independent sinusoidal oscillators 26.1 to 26.6. Each of the sinusoidal oscillators 26.1 to 26.6 are calibrated by means of adjustment screws 49 and 50. Adjustment screw 49 will adjust the frequency signal whilst the adjustment screw 50 will adjust the amplitude of the signal whereby the outputs 30.1 to 30.6 of the oscillators will contain a pure test tone signal in accordance with ANSI Standard, S3.6-1969 (R 1973).

The time duration and time interval between the attenuated frequency signals at the output 29 of the variable attenuator 27 is selectable by means of a first and second selector switch 51 and 52 respectively. Switch 51 is a sound interval selector and is connected to a frequency divider circuit 55 which is fed at its input 54 by a master clock generator 53. The master clock generator 53 produces 400 millisecond pulses. The duration of the attenuated signals are determined by the position of switch 51. As hereinshown, there are three time duration positions pf switch 51, each position being a known multiple factor of the clock pulse. The time interval is also a multiple factor of the clock pulse. The output 56 of the frequency divider feeds the bit pattern logic circuit 42 with an interval pulse to indicate to the control circuit 16 to go for a new pattern at the end of the interval.

The frequency divider 55 feeds a "BIP" pulse at its output 77 to a pulse shaper circuit 78 driving an audio signal modulator, therein an FET switch 79. This switch 79 is used as a variable resistance to modulate the test tone of attenuated signal to the output 29, which is amplified by amplifier 80, to have a predetermined rise in amplitude at the front end thereby to prevent a transient wave which might be audible to the person undergoing the test.

The switch 81 is provided to permit insertion of a 30 dB gain in the signal at the output 29 for calibration purposes. Also, calibration variable resistors 82 are associated with each of the outputs leading to the earphones 23 and 24 to calibrate these.

Referring to FIG. 3, it can be seen that in mode I a 4 KHz frequency signal is present at the output 59 of a frequency selector. This signal is amplified by amplifier 60 and the output 61 of the amplifier 60 is connected to the variable attenuator circuit 27. With mode I, switch 28.1 of the attenuator 27 will be automatically activated whereby to produce an output attenuated signal of 50 dB. After the sound interval time has elapsed, switch 28.1 will be deactivated and after the elapse of the preselected interval time, switch 28.2 will be activated to produce an attenuated signal of 45 dB. This sequence will continue until switch 28.9 is activated whereby the 4 KHz signal will appear with maximum attenuation. After this last step this sequence of mode I is terminated, and the bit pattern logic circuit 42 will send an end-of-test signal, at its output 59, to the control logic circuit 15. The "ready-for-test" indicator lamp 83 will then light up.

The variable attenuator circuit 27 comprises a plurality of serially connected resistances 58 with the switches 28.1 to 28.10 being connected at the junctions of these resistances. Thus, by enabling specific ones of the switches, the signal to be transmitted is subjected to a specific attenuation.

The particular frequency signal or oscillator 26.1 to 26.6 in operation is indicated on the console (not shown) of the audiometer by a hexadecimal display device 70. In this particular case, six oscillators are to be switched in sequence and therefore, the device will indicate a letter from A to F, each of which being respectively associated with one of the oscillator circuits 26.1 to 26.6 and a corresponding marking 74 on test chart 73. Also, the console (not shown) is provided with 11 light emitting diodes 71 and respectively numbered from 1 to 11, to indicate to the person using the audiometer a position or marking 72 provided on the test chart 73, see FIG. 2. FIG. 2 shows a test chart used in conjunction with mode III. A different test chart is used for each different mode. The diodes 71 are associated with switches 28 in modes I, II and III. In modes IV and V there is no association, see FIG. 3. The buffer circuit 97 interconnects the various signals from the manual switch or automatic selection by the generator 16, to the lamps 70, 71, 83, 84 and 85.

The user fills in the test chart appropriate to the mode being used when instructed to do so and where to do so, by instruction from the lamps 70, 71, 83, 84 and 85. For example, in mode III when the user starts the test on his left ear and first hears a test tone from frequency signal A and the eleventh diode is lit, he will put an "X" mark in the eleventh square 72 on chart 73 in the "A" column. The person undergoing testing will continue to fill this chart when he hears test tones for all frequencies of the mode being used and until the entire mode of operation has terminated for the section 75 of the chart marked left ear. The user will then enable the right ear switch 17 on the console and the mode of operation will again commence with the user writing his responses through the sequence of section 76 of the test chart. Thus, the appropriately completed test chart will provide the information to evaluate the hearing acuity of a person's left and right ears.

A further lamp 84 is provided on the console to indicate that the signal is being transmitted to the left ear and a lamp 85 indicates that the signal is being transmitted to the right ear.

A sub-mode selector switch 86 is provided to preselect the modes to operate with a group of three frequencies or all six frequencies depending on the switch position. Switch position 87 will limit the frequencies of modes II, III and IV to a group of three frequencies while switch position 88 will select all six frequencies from the frequency source 26. The output 89 of the switch 86 connects to the bit pattern logic circuit 42 to instruct the generator 16.

For calibration purposes, a switch 90 connects to the bit pattern logic circuit 42 and the switch is normally in its automatic position 91 where the control circuit 16 operates automatically. For calibration purposes, the switch 90 may be switched to a manual position 92 for calibrating individual frequencies. Switch 96 will step the frequency selector in the manual position of switch 90.

The pattern generator 44 will operate modes I, II and V. Mode I was described above. Mode II goes sequentially through a group of three or all the frequency sources 26.1 to 26.6 depending on the selection made by switch 86, and the attenuator is also operated in a progressive sequence of attenuation from 50 dB down to 10 dB in 5 dB steps. Mode V is a fixed mode where each frequency signal is attenuated once at the same level.

The pattern generator circuit 43 is associated with mode III wherein the system will connect all six frequencies to the variable attenuator 27 and go through each level 28 of attenuation but in a variable random pattern. In the setting shown in FIG. 3, the first attenuation will be 50 dB, the second will be 35, the third will be NIL (that is no signal at all) and so forth. Thus, a partially hard of hearing person undergoing the test in this mode cannot cheat by indicating on the chart 73 that he has heard all frequencies corresponding, for example, to indicator lights 71 numbered 2 to 8 (as would be possible with mode II) since he has no clue to the level being sent to his ear.

The mode IV pattern generator 45 will transmit in rapid succession a group of three or all six frequencies at one single attenuated level. FIG. 3 shows mode IV set for a fixed 20 dB level. This level is preselected by adjusting a mechanical level selector switch 95 which is inside the console and not accessible to the person using the audiometer. Also, all calibrating switches as well as switches 51, 52, 40 and 86 are not accessible to the person undergoing the test.

In summary, the audiometer of the present invention provides a method of testing the hearing of a person wherein the audiometer is preset by switch 40 to operate automatically in a preselected mode of operation which automatically selects a plurality of fixed frequency signals 26.1 to 26.6 in a predetermined time sequence determined by the setting of switches 51 and 52. Each of these signals is then automatically attenuated by predetermined attenuation levels 28 in attenuator 27 in a preselected manner depending on the mode of operation selected. Each of the attenuated frequency signals, having a preselected time duration and preselected time interval between them, are transmitted to selected ones of a pair of earphones 23 and 24 whereby to subject the person to an auditory acuity test of his left or right ear. The particular frequency signal being transmitted is indicated on the console (not shown) by lamps 70. Each of the attenuated frequency signals being transmitted to the earphones are indicated by lamps 71. This permits the user to locate on a test chart 73 the sounds that are audible to his ears. Thus, the person fills out the chart 73 and this represents the information for the diagnosis of the auditory acuity of his ears.

It is within the ambit of the present invention to cover any obvious modifications of the invention provided these fall within the broad definition of the invention defined by the claims. For example, the audio generator (frequency source 26) could also be formed of one frequency programmable oscillator or other suitable means. Also, the frequency selector circuit 25 could be designed differently and the attenuator circuit 27 could be constituted by a different design or use an amplitude programmable oscillator or other suitable means. Further instead of earphones 23 and 24, the signals could be sent through loudspeakers or a bone vibrator. The visual display could also be provided by other means such as LCD's or even filament lamps.

We claim:

1. An audiometer for testing the hearing of a person, said audiometer comprising a source of audible and selectable fixed frequency signals, frequency selector means for selecting a predetermined frequency signal from said source, a variable attenuator circuit having a plurality of attenuation levels for automatically attenuating said predetermined frequency signal through said attenuation levels and according to a preselected mode of operation for transmission of a plurality of attenuated frequency signals, means to transmit said attenuated frequency signals for audible reception by said person, visual display means to indicate the transmission of each of said attenuated frequency signals, and control circuit means for enabling said frequency selector means and said variable attenuator in accordance with said preselected mode of operation.

2. An audiometer as claimed in claim 1 wherein said control circuit means is a bit pattern generator having pattern generator circuits associated with respective modes of operation and actuable by mode selecting switch means to cause said frequency selector means and variable attenuator to operate in a predetermined manner.

3. An audiometer as claimed in claim 2 wherein said pattern generator circuits provide automatic sequential step operation of said frequency selector means for transmitting all or a group of said fixed frequency signals in sequential order and within predetermined time delays while enabling said variable attenuator circuit to switch to predetermined ones of said attenuation levels of said preselected mode of operation during transmission of each frequency signal of said all or a group of said fixed frequency signals.

4. An audiometer as claimed in claim 3 wherein one of said generator circuits is programmed to enable said variable attenuator circuit to switch to said attenuation levels in a predetermined random manner whereby said person will be subjected to signals of random attenuated levels.

5. An audiometer as claimed in claim 3 wherein a first selector switch is provided to preselect the duration of each said attenuated frequency signals, and a second selector switch to preselect the duration of time intervals between each of said attenuated frequency signals.

6. An audiometer as claimed in claim 5 wherein one of said generator circuits is provided with level selector switches to manually select a single level of attenuation for each of said fixed frequency signals.

7. An audiometer as claimed in claim 3 wherein there is further provided a visual indicator signal to identify the particular attenuated frequency signal being transmitted, and a test chart for use by said person, said test chart having individual markings to identify all of said attenuated frequency signals associated with each frequency signal of said source whereby said person can indicate on said chart which ones of all transmitted attenuated frequency signals of said group is audible to him.

8. An audiometer as claimed in claim 5 wherein said bit pattern generator further comprises a bit pattern logic circuit through which said pattern generator circuits are selected, said bit pattern generator being enabled by a start pulse from a control logic circuit, said control logic circuit actuating an analog switch associated with said person's left or right ear.

9. An audiometer as claimed in claim 8 wherein said mode selecting switch means is a selector switch connected to said bit pattern logic circuit to select said pattern generator circuits, and a sub-mode selector switch also connected to said bit pattern logic circuit to enable selection of all or a group of said fixed frequency signals in each of said modes of operation.

10. An audiometer as claimed in claim 9 wherein said source of audible and selectable fixed frequency signals comprises six independent sinusoidal oscillators each producing a pure test tone.

11. An audiometer as claimed in claim 10 wherein said frequency selector means consists of six analog switches each of which is connected to a respective output of an associated one of said oscillators.

12. An audiometer as claimed in claim 11 wherein said variable attenuator circuit comprises a plurality of serially connected resistances with automatically operable switches at the junctions of said resistances, each said switches being actuable to switch "on" and "off" for predetermined times selected by said first and second selector switches in a sequence determined by said selected mode of operation whereby to produce said attenuated frequency signals for audible reception, said oscillators being selected automatically by said control circuit means.

13. An audiometer as claimed in claim 12 wherein said means to transmit said attenuated frequency signals for audible reception by said person is constituted by a pair of earphones.

14. An audiometer as claimed in claim 12, wherein said visual display means comprises a plurality of light emitting diodes, each of said diodes being enabled simultaneously with the operation of an associated one of said automatically operable switches, said diodes providing a signal to said person to indicate an association between said individual markings on said chart and said attenuated frequency signals, said visual display means comprising a hexadecimal display device.

15. An audiometer as claimed in claim 12 wherein calibrating circuits are associated with said control circuit means, each of said oscillators, and said means to transmit said attenuated frequency signal.

16. An audiometer as claimed in claim 6 wherein said audiometer is operable by said person, said audiometer being automatically operable upon activation of a "power on" switch and a selection switch to direct said attenuated frequency signals to a selected ear of said person.

17. An audiometer as claimed in claim 5 wherein said first and second selector switches are connected to a frequency divider circuit fed by a master clock generator to produce a signal that drives an audio signal modulator according to said preselected duration and time interval by said first and second selector switches, respectively, said frequency divider being connected to said bit pattern logic circuit to instruct said bit pattern logic circuit to release a new pattern at the end of said time interval.

18. A method of testing the hearing of a person comprising the steps of:
(i) automatically selecting in a preselected mode of operation a plurality of fixed frequency signals,
(ii) automatically attenuating each of said fixed frequency signals by a plurality of attenuating levels preselected in accordance with said mode of operation to produce a plurality of attenuated frequency signals,
(iii) transmitting each said attenuated frequency signal to a selected one of said person's ears to provide to said person a means of self determining the auditory acuity of his ears, and
(iv) visually indicating a selected one of said fixed frequency signals and each of said attenuated frequency signals or steps of attenuation being transmitted.

19. A method as claimed in claim 18 wherein step (ii) includes selecting a predetermined mode of operation from a plurality of modes of operation and providing a test chart associated with said selected mode of operation whereby said person will record on said chart each of said attenuated frequency signals audibly perceived.

20. A method as claimed in claim 19 wherein said step (ii) comprises means of automatically attenuating each of said frequency signals by predetermined random attenuating levels.

* * * * *